United States Patent
Yoshida et al.

(12)

(10) Patent No.: US 6,307,104 B1
(45) Date of Patent: Oct. 23, 2001

(54) PROCESS FOR PRODUCING A PRIMARY AMINE COMPOUND

(75) Inventors: Wataru Yoshida; Tetsuaki Fukushima, both of Wakayama (JP)

(73) Assignee: Kao Corporation, Tokyo (JP)

( * ) Notice: Subject to any disclaimer, the term of this patent is extended or adjusted under 35 U.S.C. 154(b) by 0 days.

(21) Appl. No.: 09/552,659

(22) Filed: Apr. 19, 2000

(30) Foreign Application Priority Data

May 6, 1999 (JP) .................................................. 11-125914

(51) Int. Cl.[7] .................................................. C07C 209/48
(52) U.S. Cl. .................................................. 564/493
(58) Field of Search .................................................. 564/493

(56) References Cited

U.S. PATENT DOCUMENTS 4,153,578   5/1979   De Thomas, et al. .
4,248,799 * 2/1981   Drake .................................. 564/491
5,840,989 * 11/1998  Cordier et al. ........................ 564/490

FOREIGN PATENT DOCUMENTS 2 722 709   1/1996   (FR) .
2 722 710   1/1996   (FR) .

OTHER PUBLICATIONS

Database CAPLUS on STN, Acc. No. 1991:679185, Besson et al., 'Structure and catalytic properties in hydrogenation of valeronitrile of Raney nickel prepared from chromium and molybdenum doped nickel–aluminum (Ni2A13) alloys.' Stud. Surf. Catal. (1991), 59 (Heterog. Catal. Fine Chem. 2) pp. 113–120 (Abstract).*

* cited by examiner

*Primary Examiner*—Johann Richter
*Assistant Examiner*—Brian J. Davis
(74) *Attorney, Agent, or Firm*—Oblon, Spivak, McClelland, Maier & Neustadt, P.C.

(57) ABSTRACT

The present invention relates to a process for producing both of a primary amine compound and an alkylene oxide adduct thereto, given that the both are excellent in color, with high yield. That is, the process comprises hydrogenating a nitrile compound in the presence of a Raney catalyst comprising 90 to 96% by weight of Ni, 3 to 9% by weight of Al and 0.5 to 3% by weight of Mo being based on the total of the atoms of Ni, Al and Mo to obtain the primary amine compound. Further, an alkylene oxide may be added thereto to obtain an alkylene oxide adduct to the primary amine compound.

6 Claims, No Drawings

PROCESS FOR PRODUCING A PRIMARY AMINE COMPOUND

TECHNICAL FIELD

The invention relates to both of a process for producing a primary amine compound and an alkylene oxide adduct thereto, given that the both are excellent in color.

PRIOR ARTS

An aliphatic primary amine compound and an alkylene oxide adduct thereto are important compounds in the field of products of household and industrial uses. In particular, they are used as starting materials for manufacturing surfactants, intermediates for fiber treatments and for bactericidal substances, and then active components of insecticides and of fiber softeners. In these applications, it is desirable that the amine compound and the adduct thereof are very pure and colorless substances.

Conventionally the primary amine compound can be obtained by hydrogenating a nitrile with a Raney nickel or a Raney cobalt as catalyst. Those methods are provided with a decreased selectivity of amine and an obtainable production yield not being sufficient. The color is not sufficient, either. The alkylene oxide adduct which is obtained from the primary amine compound as starting material of the adduct has also a color not being sufficient.

DISCLOSURE OF THE INVENTION

The purpose of the present invention is to provide a process for producing both of a primary amine and an alkylene oxide adduct thereto, given that the both are excellent in color, with high yield.

The present invention provides a process for producing a primary amine compound, comprising hydrogenating a nitrile compound in the presence of a Raney catalyst comprising 90 to 96% by weight of Ni, 3 to 9% by weight of Al and 0.5 to 3% by weight of Mo being based on the total of the atoms of Ni, Al and Mo. It then provides the process which further comprises adding an alkylene oxide to obtain an alkylene oxide adduct to the primary amine compound as defined above.

Incidentally, the Raney catalyst in the present invention may be an alloy having activity as catalyst for hydrogenating, which is obtained by eroding an alloy of a metal (A) having activity as catalyst for hydrogenating and another metal (B) by means of an eroding agent such as water, an alkali, an acid and the like to properly eliminate (B) (this procedure or operation is referred to development).

It is preferable that a weight ratio of Al/Ni ranges from 0.02 to 0.09; Mo/Ni ranges from 0.001 to 0.03; and Mo/(Ni+Al) ranges from 0.005 to 0.03.

The primary amine compound of the present invention is excellent in color and contains a reduced amount of non-amines. Further, it is preferable that the obtained amine compound has unsaturation.

The present invention further provides use of the amine compound as obtained by the process as defined above for producing an alkylene oxide adduct thereto.

DETAILED EXPLANATION OF INVENTION

A catalyst used in the present invention is a Raney catalyst comprising 90 to 96% by weight of Ni, 3 to 9% by weight of Al and 0.5 to 3 % by weight of Mo being based on the total of the atoms of Ni, Al and Mo. Outside the above shown ranges of Ni, Al and Mo, a reaction rate decreases, an amount of containable non-amines increases and the obtainable amine compound gets worse in color.

It is preferable that a weight ratio of Al/Ni ranges from 0.02 to 0.09, in particular from 0.03 to 0.08; Mo/Ni ranges from 0.001 to 0.03, in particular from 0.01 to 0.02; and Mo/(Ni+Al) ranges from 0.005 to 0.03, in the catalyst.

The catalyst used in the invention can be prepared, for example, by adding a molybdenum compound such as ammonium molybdate to an aqueous slurry of a commercially available Raney nickel catalyst and stirring to deposit the molybdenum compound on the Raney nickel catalyst or by etching an alloy of nickel, molybdenum and aluminum with an alkali.

In the present invention, the catalyst may be preferably added in an amount of 0.05 to 1.00% by weight to the nitrile.

The starting nitrile used in the present invention is preferably a saturated or unsaturated aliphatic nitrile compound having 8 to 36 carbon atoms. It includes, for example, caprylonitrile, lauronitrile, palmitonitrile, stearonitrile and oleonitrile.

Hydrogenation of the present invention may be preferably carried out under the hydrogen pressure of 0.05 to 50 Mpa at the reaction temperature of 60 to 160° C. The obtained primary amine compound may be purified, for example, by distillation.

An alkylene oxide adduct having an excellent color is obtained, when an alkylene oxide is added to the primary amine compound, as starting material, obtained by the above-mentioned process.

The alkylene oxide used in the present invention includes ethylene oxide, propylene oxide and butylene oxide. Ethylene oxide and propylene oxide are preferable. Ethylene oxide is particularly preferable. The mole number of added alkylene oxide is preferably 1 to 30 moles to 1 mole of the primary amine.

In the present invention, an addition reaction of an alkylene oxide can be carried out under reaction conditions for normal addition reaction of an alkylene oxide, preferably at the reaction temperature of 120 to 180° C.

As obviously disclosed by the following examples, the present invention provides a process which can unexpectedly improve productivity as compared with that of conventional arts and which can produce a primary amine compound, with high yield, having high quality such as being excellent in color and containing a reduced amount of contained non-amines. Further, in the case of producing unsaturated amine compounds, retention of the iodine value (as referred to IV, hereinafter) is improved but had been hardly improved. And then, unsaturated amine compounds can be produced with high selectivity and high yield. Furthermore, quality of derivatives formed by using the obtained amine compound becomes excellent in color. In particular, quality of amine derivatives obtained by adding an alkylene oxide thereto becomes as well.

EXAMPLES

In examples, % is based on weight without special note.

Preparation Example 1 of the Catalyst 13.5 g of solid ammonium molybdate, as $(NH_3)_6Mo_7O_{24} \cdot 4H_2O$, were added to 20.0 g of an aqueous slurry of a commercially available Raney nickel containing about 50% by weight of nickel powder. The resultant mixture was stirred for 24 hours. Then, the resultant dispersion was washed twice with 20 mL of water. The solid part was analyzed in view of composition. Catalyst A was obtained, having the composition shown in Table 1.

Preparation Example 2 of the Catalyst

Catalyst B was obtained, having the composition shown in Table 1, in the same manner as Preparation Example 1 except for changing kinds of the Raney nickel and the amount of ammonium molybdate.

Preparation Examples 3 to 4 of the Catalyst

Catalysts C and D were obtained, having the composition shown in Table 1, by etching various kinds of commercially available alloys of nickel, molybdenum and aluminum having different compositional proportions with an alkali and then analyzing the solid part in view of composition.

Comparative Catalyst

Commercially available Raney nickel catalysts having the composition shown in Table 1 were used as Comparative Catalysts a and b.

the hydrogen gas was no longer absorbed. The reaction system was aged further for 15 minutes. Absorption of hydrogen gas proceeded smoothly and the absorption was completed in 0.8 hour. After finish of the reaction and aging, the reaction product was taken out from the reactor and the catalyst was removed off. Then, the reaction product was distilled and purified under 0.27 kPa at 220° C. Stearylamine was obtained with yield of 94%.

The obtained stearylamine was measured in view of the amount of the contained non-amines and color by the below described methods. Results are shown in Table 2.

<Amount of Contained Non-amines>

The obtained stearylamine was measured in view of the amount of the contained non-amines by the method described in AOCS official method Tw 1a-64, Percent Non-Amines in Fatty Amines and Diamine.

<Color>

The obtained stearylamine was observed to measure color using an APHA tube, just after distillation and after that the stearylamine had been quietly laid at 160° C. under stream of nitrogen gas for 2 hours (from the distillation). Incidentally, the method for measuring APHA was carried out according to AOCS Td 1b-64T.

Examples 2 to 4 and Comparative Examples 1 to 2

Stearylamine was obtained in the same manner as shown in Example 1 except for reaction conditions shown in Table 2, using Catalyst B, C or D of the present invention or Comparative Catalyst a or b in place of Catalyst A. It was measured in view of the amount of the contained non-amines and color in the same manner as shown in Example 1. Results are shown in Table 2.

TABLE 1

|  | Catalysts of the present invention | | | | Comparative Catalysts | |
| --- | --- | --- | --- | --- | --- | --- |
|  | Catalyst A | Catalyst B | Catalyst C | Catalyst D | Catalyst a | Catalyst b |
| Composition of catalysts (%) | | | | | | |
| Ni | 95.5 | 93.6 | 92.8 | 92.1 | 95.6 | 94.2 |
| Al | 4.0 | 5.0 | 5.8 | 5.3 | 4.4 | 5.8 |
| Mo | 0.5 | 1.4 | 1.4 | 2.6 | 0 | 0 |
| Weight ratio of Al/Ni | 0.042 | 0.053 | 0.063 | 0.057 | 0.046 | 0.062 |
| Weight ratio of Mo/Ni | 0.005 | 0.015 | 0.015 | 0.028 | 0 | 0 |

Incidentally, nickel of the catalyst was analyzed by titration with an EDTA solution using murexide indicator. Aluminum was analyzed by titration with an EDTA solution using Cu-Pan indicator. Molybdenum was analyzed by atomic absorption analysis (method of standard addition).

Example 1

300 g of stearonitrile were fed into a 1 liter autoclave and then 3 g of Catalyst A, 12 g of water and 1 g of 48% sodium hydroxide were put thereinto. After purging with nitrogen gas, the reaction was carried out under the hydrogen pressure of 2.0 MpaG at the reaction temperature of 120° C. The reaction-finishing point was determined at the point where

TABLE 2

| | | Reaction condition for hydrogenation | | | Amount of the | Amine compound after purification | | |
|---|---|---|---|---|---|---|---|---|
| | | | | | | | Color (APHA) | |
| | Catalyst | Temperature of reaction (° C.) | Time of reaction*1 (Hr) | Yield of distillation (%) | contained non-amines (%) | | Just after distillation | 2 hours after distillation |
| Examples | | | | | | | | |
| 1 | A | 120 | 0.8 | 94 | 0.28 | | <5 | 30 |
| 2 | B | 120 | 0.4 | 96 | 0.11 | | <5 | 5 |
| 3 | C | 120 | 0.5 | 95 | 0.09 | | <5 | 5 |
| 4 | D | 120 | 1.0 | 96 | 0.20 | | <5 | 10 |
| Comparative Examples | | | | | | | | |
| 1 | a | 120 | 1.5 | 90 | 0.43 | | <5 | 40 |
| 2 | b | 120 | 2.0 | 91 | 0.69 | | 5 | 50 |

*1: not including aging for 15 minutes.

Example 5

300 g of oleonitrile were fed into a 1 liter autoclave and 2 g of Catalyst A, 6 g of water and 0.5 g of 48% sodium hydroxide were put thereinto. After purging with nitrogen gas, the reaction was carried out under the hydrogen pressure of 1.0 MpaG at the reaction temperature of 130° C. The reaction-finishing point was determined at the point where the hydrogen gas was no longer absorbed. The reaction system was aged further for 15 minutes. Absorption of hydrogen gas proceeded smoothly and the absorption was completed in 1.3 hour. After finish of the reaction and aging, the reaction product was taken out from the reactor and the catalyst was removed off. Then, the reaction product was distilled and purified under 0.27 kPa at 220° C. Oleylamine was obtained with yield of 94%.

The obtained oleylamine was measured in view of the amount of the contained non-amines and color in the same manner as shown in Example 1. Further, the starting nitrile and the oleylamine obtained just after the distillation were measured in view of an iodine value (IV). Retention of IV was determined with the below shown equation. Results are shown in Table 3.

$$\text{Retention of IV (\%)} = \frac{\text{IV of amine after distillation}}{\text{IV of starting nitrile}} \times 100$$

Examples 6 to 8 and Comparative Examples 3 to 4

Oleylamine was obtained in the same manner as shown in Example 5 except for reaction conditions shown in Table 3, using Catalyst B, C or D of the present invention or Comparative Catalyst a or b in place of Catalyst A. The obtained oleylamine was measured in view of the amount of the contained non-amines, retention of IV and color in the same manner as shown in Example 5. Results are shown in Table 3.

TABLE 3

| | | Reaction condition for hydrogenation | | | Quality of amine compound after purification | | | |
|---|---|---|---|---|---|---|---|---|
| | | | | | Amount of | | Color (APHA) | |
| | Catalyst | Temperature of reaction (° C.) | Time of reaction*1 (Hr) | Yield of distillation (%) | contained non-amines (%) | Retention of IV (%) | Just after distillation | 2 hours after distillation |
| Example | | | | | | | | |
| 5 | A | 130 | 1.3 | 94 | 0.65 | 83 | 5 | 50 |
| 6 | B | 130 | 0.5 | 96 | 0.48 | 86 | 5 | 30 |
| 7 | C | 130 | 0.8 | 93 | 0.87 | 84 | 5 | 40 |
| 8 | D | 130 | 1.4 | 96 | 0.65 | 87 | 5 | 20 |

TABLE 3-continued

| | | Reaction condition for hydrogenation | | | Quality of amine compound after purification | | | |
|---|---|---|---|---|---|---|---|---|
| | Catalyst | Temperature of reaction (° C.) | Time of reaction*1 (Hr) | Yield of distillation (%) | Amount of contained non-amines (%) | Retention of IV (%) | Color (APHA) Just after distillation | 2 hours after distillation |
| Comparative Examples | | | | | | | | |
| 3 | a | 130 | 2.4 | 87 | 1.12 | 72 | 10 | 100 |
| 4 | b | 130 | 3.0 | 88 | 1.32 | 79 | 5 | 80 |

*1: not including aging for 15 minutes

Examples 9 to 12 and Comparative Examples 5 to 6

300 g (1.13 mol) of stearylamine, obtained in Examples 1 to 4 Comparative Examples 1 to 2, were fed into a 1 liter autoclave with a stirrer. After purging with nitrogen gas, the reaction system was heated up to 180° C. 107 g of ethylene oxide (EO) were forced to be pressed thereinto with the rate of 10 g per minute at a constant temperature. The ratio by mole of the amine to EO was 1/2.15. After finish of feeding, the reaction system was aged for 30 minutes. And then, the product of ethylene oxide adduct to stearylamine was taken out from the reactor. The obtained ethylene oxide adduct was measured in view of color, when the adduct was just obtained and when the adduct had been kept at 80° C. under stream of nitrogen gas for 20 days, in the same manner as shown in Example 1. Further, the obtained ethylene oxide adduct was observed to measure turbidity. Results are shown in Table 4.

TABLE 4

| | | | Ethylene oxide adduct | | |
|---|---|---|---|---|---|
| | | Starting amine | Color (APHA) Just after production | 20 days after production | Turbidity |
| Examples | 9 | Example 1 | 30 | 50 | Clear. |
| | 10 | Example 2 | 10 | 20 | Clear. |
| | 11 | Example 3 | 15 | 30 | Clear. |
| | 12 | Example 4 | 20 | 30 | Clear. |
| Comparative Examples | 5 | Comparative Example 1 | 50 | 150 | Clear. |
| | 6 | Comparative Example 2 | 40 | 80 | Turbid. |

Examples 13 to 16 and Comparative Examples 7 to 8

An ethylene oxide (EO) adduct to oleylamine was obtained in the same manner as shown in Example 9 except for using 300 g (1.09 mol) of oleylamine obtained in Examples 5 to 8 and Comparative Examples 3 to 4 in place of stearylamine and forcing to press 103 g of ethylene oxide at the rate of 10 g per minute at a constant temperature. The obtained ethylene oxide adduct was measured in view of color and turbidity in the same manner as shown in Example 9. Results are shown in Table 5.

TABLE 5

| | | | Ethylene oxide adduct | | |
|---|---|---|---|---|---|
| | | | Color*1 (APHA) | | |
| | | Starting amine | Just after production | 20 days after production | Turbidity |
| Examples | 13 | Example 5 | 50 | 200 | Clear. |
| | 14 | Example 6 | 40 | 150 | Clear. |
| | 15 | Example 7 | 60 | G1 | Clear. |
| | 16 | Example 8 | 40 | 150 | Clear. |
| Comparative Examples | 7 | Comparative Example 3 | 100 | G3 | Turbid. |
| | 8 | Comparative Example 4 | G2 | G5 | Turbid. |

*1 G is Gardner color.

What is claimed is:

1. A process for producing a primary amine compound, comprising hydrogenating a nitrile compound in the presence of a Raney catalyst comprising 90 to 96% by weight of Ni, 3 to 9% by weight of Al and 0.5 to 3% by weight of Mo being based on the total of the atoms of Ni, Al and Mo, in which a weight ratio of Mo/Ni ranges from 0.001 to 0.03.

2. The process as claimed in claim 1, which further comprises adding an alkylene oxide to obtain an alkylene oxide adduct to the amine compound as defined in claim 1.

3. The process as claimed in claim 1, in which a weight ratio of Al/Ni ranges from 0.02 to 0.09; Mo/Ni ranges from 0.001 to 0.03; and Mo/(Ni+Al) ranges from 0.005 to 0.03.

4. The process as claimed in claim 1, in which the obtained amine compound has unsaturation.

5. The process of claim 1, wherein a weight ratio of Mo/Ni ranges from 0.01 to 0.02.

6. The process of claim 1, which comprises 1.4 to 2.6% by weight of Mo.

* * * * *